(12) United States Patent
Choi

(10) Patent No.: US 8,771,976 B2
(45) Date of Patent: Jul. 8, 2014

(54) METHOD OF CANCER DIAGNOSIS USING THE ANALYSIS OF ISOTOPES

(76) Inventor: Won Cheol Choi, Incheon (KR)

( * ) Notice: Subject to any disclaimer, the term of this patent is extended or adjusted under 35 U.S.C. 154(b) by 1090 days.

(21) Appl. No.: 12/674,425

(22) PCT Filed: Oct. 17, 2007

(86) PCT No.: PCT/KR2007/005088
§ 371 (c)(1),
(2), (4) Date: Feb. 20, 2010

(87) PCT Pub. No.: WO2009/028760
PCT Pub. Date: Mar. 5, 2009

(65) Prior Publication Data
US 2013/0177936 A1     Jul. 11, 2013

(30) Foreign Application Priority Data

Aug. 27, 2007   (KR) .................. 10-2007-0085873

(51) Int. Cl.
*C12Q 1/06* (2006.01)
*B01D 59/44* (2006.01)
*G01N 33/574* (2006.01)
*C12Q 1/04* (2006.01)
*G01N 33/49* (2006.01)
*G01N 33/84* (2006.01)

(52) U.S. Cl.
CPC .......... *G01N 33/49* (2013.01); *G01N 33/57446* (2013.01); *G01N 33/57423* (2013.01); *C12Q 1/04* (2013.01); *G01N 33/57415* (2013.01); *G01N 33/57438* (2013.01); *G01N 33/57426* (2013.01); *G01N 33/84* (2013.01)

USPC ............................................ 435/34; 250/282

(58) Field of Classification Search
CPC ........................... C12M 1/343; C12M 1/3438
See application file for complete search history.

(56) References Cited

U.S. PATENT DOCUMENTS

2003/0211036 A1   11/2003   Degani et al.

FOREIGN PATENT DOCUMENTS

| JP | 2005-121622 A | 5/2005 |
| WO | 2005/070438 A1 | 8/2005 |
| WO | WO 2006107814 A2 * | 10/2006 |

OTHER PUBLICATIONS

Arneson, L.S., and MacAvoy, S.E. "Carbon, nitrogen, and sulfur diet-tissue discriminiation in mouse tissues", Canadian Journal of Zoology 2005, vol. 83, pp. 989-995.*
Prohaska, T., Latkoczy, C., and Stingeder, G. "Precise sulfur isotope ratio measurements in trace concentration of sulfur by inductively coupled plasma double focusing sector field mass spectrometry", Journal of Analytical Atomic Spectrometry 1999, vol. 14, pp. 1501-1504.*
International Search Report from PCT/KR2007/005088 mailed May 16, 2008.

* cited by examiner

*Primary Examiner* — Allison Ford
*Assistant Examiner* — Michelle F Paguio Frising
(74) *Attorney, Agent, or Firm* — Hultquist, PLLC; Mary B. Grant

(57) ABSTRACT

Disclosed is a method of diagnosing cancer on the basis of the quantitative analysis of blood or tissue isotopes. The method can accurately diagnose cancer even when it is too small for current conventional technology to diagnose.

4 Claims, No Drawings

US 8,771,976 B2

METHOD OF CANCER DIAGNOSIS USING THE ANALYSIS OF ISOTOPES

RELATED APPLICATIONS

This application is a 371 application of International Application No. PCT/KR2007/005088, filed Oct. 17, 2007, which in turn claims priority from Korean Patent Application No. 10-2007-0085873, filed Aug. 27, 2007, both of which are incorporated herein by reference in their entireties.

TECHNICAL FIELD

The present invention relates, in general, to cancer diagnosis and, more particularly, to a method for diagnosing cancer on the basis of quantitative analysis of isotopes of blood or tissue samples, which is able to accurately detect cancer even when it is too small to be detected with conventional technologies.

BACKGROUND ART

Isotopes are any of several different forms of an element each having a different atomic mass (mass number). The term "isotope", coined by British chemist F. Soddy in 1913, comes from the Greek isos "equal"+topos "place," because despite the different atomic weights, the various forms of an element occupy the same place on the periodic table.

Generally, the chemical properties of an element depend on the number of protons, that is, the atomic number. Isotopes of an element have nuclei having the same number of protons (the same atomic number) but different numbers of neutrons. Therefore, isotopes have different mass numbers, which indicate the total number of nucleons—the number of protons plus neutrons.

For example, oxygen occurs in nature as three different isotopes, each with 8 protons. The most common isotope is $^{16}O$ (8 protons, 8 neutrons), which constitutes more than 99% of all oxygen atoms on earth. There is also the rare isotope $^{18}O$ (10 neutrons) and the even rarer isotope $^{17}O$ (9 neutrons). Nitrogen exists as two stable isotopes, $^{14}N$ and $^{15}N$, in nature. Naturally occurring uranium is composed of three major isotopes, uranium-238, uranium-235, and uranium-234.

Because there are the same numbers of electrons as protons in an element, isotopes of an element are identical in the number of electrons. Approximately 90 elements exist in nature, and there are as many as about 300 naturally occurring isotopes, with an average of 3 isotopes per element. In fact, tin (Sn) is the element with the greatest number of stable isotopes (ten), and cadmium has the second highest number of isotopes (eight) while there are elements that exist as only one isotope in nature, such as beryllium, fluorine, sodium and bismuth.

There is no general rule for relationship between a naturally occurring element and the number of stable isotopes thereof. However, it has been observed that most of the elements that have odd atomic numbers each have two or fewer isotopes, whereas individual elements with even atomic numbers have relatively many isotopes. A naturally occurring element is a mixture of isotopes with almost the same ratios therebetween or thereamong in any sample of the earth. In general, the atomic weight of an element is the average of the atomic masses of all the chemical element's isotopes as found in a particular environment, weighted by isotopic abundance. The reason why a majority of atomic weights are not integers or near-integers but decimals is that most elements are assemblages of isotopes. For a short-hand designation of different isotopes (also called nuclides), the mass number (number of nucleons) is written in the right position or in the upper left corner of the chemical symbol, like oxygen-16, $^{16}O$, nitrogen-14 $^{14}N$, uranium-235 $^{235}U$, etc. Particularly as for hydrogen isotopes, specific names are given thereto, such as protium for H-1, deuterium for H-2, and tritium for H-3.

Recent studies have showed that the oxygen isotope $^{18}O$ is toxic to organisms. Deuterium $^{2}H$ in the form of $D_2O$ was found to have 92% inhibitory activity against microorganisms and to kill rats at a rate of 99.5% within 5 days.

High prevalence rates of cancer are reported in radioactive contamination area, implying that persons excessively exposed to radioactive radiation may increase in isotope level in their bodies and may be liable to affliction with cancer.

Leading to the present invention, intensive and thorough research into the treatment and diagnosis of cancer, conducted by the present inventor, resulted in the finding that cancer can be caused with a change in blood isotope level and that the incidence and kind of cancer can be diagnosed through the quantitative analysis of blood or tissue isotopes.

DISCLOSURE

Technical Problem

The present invention pertains to cancer diagnosis through the analysis of blood or tissues for isotope content. It is difficult for even up-to-date scientific technology to accurately diagnose tumors less than 1 mm in size. However, blood analysis according to the present invention can provide a basis or criteria with which accurate diagnosis can be achieved for the incidence and kind of cancer in an early stage, thus giving rise to an increase in the probability of successful cancer treatment. Therefore, it is an object of the present invention to provide a method of diagnosing cancer by analyzing blood or tissue isotope levels and comparing them with those of normal persons.

Technical Solution

In order to accomplish the above object, the present invention provides a method of diagnosing cancer, comprising measuring levels of isotopes of an element in a blood sample or a tissue sample.

In accordance with a modification thereof, the element is selected from a group consisting of hydrogen, oxygen, magnesium, calcium, potassium, sulfur, chloride, silicon, iron, copper, and combinations thereof.

In accordance with another modification thereof, the method is based on an increase in the level of deuterium ($^{2}H$) by 10% or higher compared to a normal standard.

In accordance with a further modification, the method is based on an increase in the level of $^{18}O$ by 10% or higher, compared to a normal standard.

In accordance with still a further modification, the method is based on an increase in the level of a heavy isotope of the element compared to a normal standard.

In accordance with still another modification, the method is based on the depletion of $^{40}K$ and/or $^{36}S$ from the sample.

Advantageous Effects

Featuring the quantitative analysis of blood or tissue isotopes, the present invention can accurately diagnose cancer even when it is too small for current conventional technology to diagnose. Hence, the present invention can make a great contribution to the treatment of cancer and provide an opportunity for cancer patients to recover from the disease and lead a healthy life. It is well known that when cancer is diagnosed in its early stage, it can be cured at a high success rate. However, diagnosis methods that can detect even small cancers with certainty have not been developed yet. The present invention, which overcomes the limitation of the prior art methods, can detect cancer in the early stage thereof and thus allow cancer to be successfully cured.

BEST MODE

Prior to entry into the detailed description of the present invention, it should be noted that a description of well-known functions or constitutions in conjunction with the present invention will be omitted in order to make the gist of the present invention unambiguous.

In the present invention, distilled water, mineral water, electrolysed water, and blood and tissues from healthy persons and cancer patients are qualitatively and quantitatively analyzed for isotopes. An example of an instrument for use in the isotope analysis includes EMAL-2 (Energy Mass Analyzer), which is a double-focus type mass spectrophotometer. Individual ions are used as laser sources for atomic ionization and vaporization.

A standard sample is used to correct the analysis results. In this regard, 10 elements, including magnesium, silicon, sulfur, chloride, potassium, calcium, chrome, iron, copper, hydrogen, and oxygen, are employed and analyzed for compositions in various samples. Stable isotopes analyzed in the present invention have mass numbers 24, 25 and 26 for the element magnesium, mass numbers 28, 29 and 30 for the element silicon, mass numbers 32, 33, 34 and 36 for the element sulfur, mass numbers 35 and 37 for the element chloride, mass numbers 39, 40 and 41 for the element potassium, mass numbers 40, 42, 43, 44, 46 and 48 for the element calcium, mass numbers 50, 52, 53 and 54 for the element chrome, mass numbers 54, 56, 57 and 58 for the element iron, and mass numbers 63 and 65 for the element copper. Prior to isotope analysis, all samples except for water are dried at 360° C. for 1 hour in a vacuum oven.

SMOW (Standard Mean Ocean Water), which serves as a reference standard for comparing hydrogen and oxygen isotope ratios, mostly in water samples, is also used in the present invention. The isotope composition of oxygen and hydrogen in a sample is expressed as per mil (‰ thousand) differences relative to SMOW. 4~5 ml of water is reacted with uranium at 800° C. in a vacuum of $10^{-5}$~$10^{-6}$ mmHg to generate hydrogen atoms for use in the measurement.

An instrument suitable for analyzing the isotope compositions of hydrogen includes a Varian GD 150 isotope ratio mass spectrometer while the isotope compositions of oxygen in water and in gas phase samples are analyzed using an Electron spectrometer (Sumi, Ukraine). These spectrometers can detect very small changes in the isotope compositions of individual elements and analyze samples and a standard simultaneously. The mass spectrometer is equipped with 2 or 3 ion collectors and can measure 2~3 ion currents at the same time and analyze the relationship therebetween. The isotope compositions of elements in blood samples are analyzed using EMAL-2.

[Mode for Invention]

A better understanding of the present invention may be obtained through the following examples which are set forth to illustrate, but are not to be construed as the limit of the present invention.

EXAMPLE 1

Deuterium Level in Blood

Deuterium content was expressed as ppm relative to protium content. Listed in Table 1 are the numbers of $^2D$ per 1,000,000 $^1H$.

TABLE 1

| Blood Samples | D/H(in ppm) |
|---|---|
| Normal | 126 |
| Stomach Cancer Patient | 147 |
| Liver Cancer Patient | 147.5 |
| Lung Cancer Patient | 148.2 |
| Breast Cancer Patient | 147.6 |
| Leukemia Patient | 148.2 |

Cancer patients were measured to have a 15~20% increase in the blood level of deuterium, compared to normal persons.

EXAMPLE 2

$^{18}O$ Level in Blood

The oxygen isotope $^{18}O$ content was expressed as ppm relative to the oxygen isotope $^{16}O$ content. Listed in Table 1 are the numbers of $^{18}O$ per 1,000,000 $^{16}O$.

TABLE 2

| Blood Samples | $^{18}O/^{16}O$(in ppm) |
|---|---|
| Normal | 1430 |
| Stomach Cancer Patient | 1998 |
| Liver Cancer Patient | 1995 |
| Lung Cancer Patient | 1994 |
| Breast Cancer Patient | 1996 |
| Leukemia Patient | 1995.5 |

Cancer patients were measured to have an about 35~40% increase in the blood level of $^{18}O$, compared to normal persons.

EXAMPLE 3

Comparison of Levels of Magnesium Isotopes in Blood

In Table 3, below, the measurements of blood magnesium isotope content using a mass spectrometer were expressed in arbitrary units.

TABLE 3

| Blood Samples | $^{24}M$ | $^{25}M$ | $^{26}M$ |
|---|---|---|---|
| Normal | 72.1 | 7.2 | 9.1 |
| Stomach Cancer Patient | 69.5 | 9.5 | 23.2 |
| Liver Cancer Patient | 45.2 | 9.6 | 45.5 |
| Lung Cancer Patient | 55.1 | 9.5 | 41.0 |
| Breast Cancer Patient | 55.6 | 15.2 | 33.2 |
| Leukemia Patient | 40.2 | 8.5 | 52.6 |

The levels of heavy isotopes in the blood were measured to be significantly increased in cancer patients, compared to normal persons.

EXAMPLE 4

Comparison of Levels of Magnesium Isotopes in Blood

In Table 4, below, the measurements of blood silicon isotope content using a mass spectrometer are expressed in arbitrary units.

TABLE 4

| Blood Samples | $^{28}Si$ | $^{29}Si$ | $^{30}Si$ |
|---|---|---|---|
| Normal | 55.2 | 10.5 | 2.2 |
| Stomach Cancer Patient | 65.3 | 25.7 | 8.6 |
| Liver Cancer Patient | 49.9 | 39.5 | 12.5 |
| Lung Cancer Patient | 59.4 | 33.4 | 13.6 |
| Breast Cancer Patient | 65.8 | 30.2 | 8.6 |
| Leukemia Patient | 65.3 | 25.6 | 10.5 |

The levels of heavy isotopes in the blood were measured to be significantly increased in cancer patients, compared to normal persons.

EXAMPLE 5

Comparison of Levels of Iron Isotopes in Blood

In Table 5, below, the measurements of blood iron isotope content using a mass spectrometer are expressed in arbitrary units.

TABLE 5

| Blood Samples | $^{54}Fe$ | $^{56}Fe$ | $^{57}Fe$ | $^{58}Fe$ |
|---|---|---|---|---|
| Normal | 3.2 | 58 | 14.1 | 2.1 |
| Stomach Cancer Patient | 3.6 | 68 | 25.1 | 3.3 |
| Liver Cancer Patient | 3.7 | 59 | 35.2 | 3.8 |
| Lung Cancer Patient | 4.1 | 63 | 28.5 | 3.5 |
| Breast Cancer Patient | 4.2 | 52 | 32.4 | 4.2 |
| Leukemia Patient | 4.2 | 60.5 | 31.5 | 3.5 |

The levels of heavy isotopes in the blood were measured to be significantly increased in cancer patients, compared to normal persons.

EXAMPLE 6

Comparison of Levels of Copper Isotopes in Blood

In Table 6, below, the measurements of blood copper isotope content using a mass spectrometer are expressed in arbitrary units.

TABLE 6

| Blood Samples | $^{63}Cu$ | $^{65}Cu$ |
|---|---|---|
| Normal | 65 | 35 |
| Stomach Cancer Patient | 72 | 28 |
| Liver Cancer Patient | 63 | 41 |
| Lung Cancer Patient | 61 | 42 |
| Breast Cancer Patient | 60 | 35 |
| Leukemia Patient | 74 | 25 |

There were no significant difference in light isotope levels between cancer patients and normal persons.

EXAMPLE 7

Comparison of Levels of Sulfur Isotopes in Blood

In Table 7, below, the measurements of blood sulfur isotope content using a mass spectrometer are expressed in arbitrary units.

TABLE 7

| Blood Samples | $^{32}S$ | $^{33}S$ | $^{34}S$ | $^{36}S$ |
|---|---|---|---|---|
| Normal | 55.5 | 20.1 | 2.3 | 1.1 |
| Stomach Cancer Patient | 62.1 | 25.5 | 9.5 | 0 |
| Liver Cancer Patient | 52.1 | 35.5 | 12.3 | 0 |
| Lung Cancer Patient | 58.9 | 26.5 | 13.2 | 0 |
| Breast Cancer Patient | 66.6 | 31.2 | 7.8 | 0 |
| Leukemia Patient | 61.2 | 25.9 | 10.3 | 0 |

The cancer patients were found to have a higher level of the heavy isotope than were normal persons. As for $^{36}S$, however, it was not detected in cancer patients, indicating that patients suffering from cancer lack the isotope.

EXAMPLE 8

Comparison of Levels of Chloride Isotopes in Blood

In Table 8, below, the measurements of blood chloride isotope content using a mass spectrometer are expressed in arbitrary units.

TABLE 8

| Blood Samples | $^{35}Cl$ | $^{37}Cl$ |
|---|---|---|
| Normal | 60.2 | 25.3 |
| Stomach Cancer Patient | 72.3 | 25.7 |
| Liver Cancer Patient | 71.5 | 28.8 |
| Lung Cancer Patient | 68.2 | 26.5 |
| Breast Cancer Patient | 77.5 | 21.3 |
| Leukemia Patient | 63.2 | 32.1 |

The overall levels of heavy isotopes in the blood were observed to be higher in cancer patients compared to normal persons.

EXAMPLE 9

Comparison of Levels of Potassium Isotopes in Blood

In Table 9, below, the measurements of blood potassium isotope content using a mass spectrometer were expressed in arbitrary units.

TABLE 9

| Blood Samples | $^{39}K$ | $^{40}K$ | $^{41}K$ |
|---|---|---|---|
| Normal | 79.5 | 1.2 | 6.3 |
| Stomach Cancer Patient | 86.4 | 0 | 10.5 |
| Liver Cancer Patient | 82.3 | 0 | 18.5 |
| Lung Cancer Patient | 94.3 | 0 | 6.5 |
| Breast Cancer Patient | 77.5 | 0 | 16.2 |
| Leukemia Patient | 88.6 | 0 | 11.1 |

Of the potassium isotopes, $^{40}K$ was measured to be zero in cancer patients, which distinguishes cancer patients from normal persons. The heavy isotope was measured at higher levels in cancer patients than in normal patients.

EXAMPLE 10

Comparison of Levels of Calcium Isotopes in Blood

In Table 10, below, the measurements of blood calcium isotope content using a mass spectrometer was expressed in arbitrary units.

TABLE 10

| Blood Samples | $^{40}Ca$ | $^{42}Ca$ | $^{43}Ca$ | $^{44}Ca$ | $^{46}Ca$ | $^{48}Ca$ |
|---|---|---|---|---|---|---|
| Normal | 57.4 | 1.2 | 2.3 | 1.7 | 0.2 | 0.15 |
| Stomach Cancer Patient | 66.8 | 3.4 | 9.5 | 6.7 | 5.7 | 1.6 |
| Liver Cancer Patient | 31.5 | 6.4 | 25.6 | 27.4 | 15.3 | 1.5 |
| Lung Cancer Patient | 54.2 | 4.6 | 18.7 | 17.5 | 7.6 | 1.2 |
| Breast Cancer Patient | 51.2 | 4.3 | 18.6 | 17.9 | 7.8 | 1.8 |
| Leukemia Patient | 34.5 | 5.6 | 19.4 | 24.6 | 15.6 | 1.1 |

The heavy isotopes of element calcium were measured at higher levels in cancer patients than in normal persons.

Taken together, the data obtained in the above examples demonstrate that the analysis of isotope levels in blood or tissues can be used to determine the incidence of cancer, particularly based on an increase in isotope levels or the depletion of $^{40}K$ or $^{36}S$.

Although the preferred embodiment(s) of the present invention have(has) been disclosed for illustrative purposes, those skilled in the art will appreciate that various modifications, additions and substitutions are possible, without departing from the scope and spirit of the invention as disclosed in the accompanying claims.

The invention claimed is

1. A method of diagnosing cancer in a patient, comprising
   (a) measuring the level of isotope $^{36}S$ in a blood sample or a tissue sample of the patient using a double-focus type mass spectrophotometer;
   (b) measuring the level of at least one of the calcium isotopes $^{42}Ca$, $^{43}Ca$, $^{44}Ca$, $^{46}Ca$ and $^{48}Ca$ in a blood sample or a tissue sample of the patient using a double-focus type mass spectrophotometer;
   (c) diagnosing cancer in the patient if (i) $^{36}S$ is not detected and (ii) the level of the at least one calcium isotope is greater than the level of a normal standard for the at least one calcium isotope.

2. The method according to claim 1, wherein the method further comprises measuring the level of $^{33}S$ in a blood sample or a tissue sample of the patient and diagnosing cancer in the patient if more than 1.3 times increased level of $^{33}S$ is detected in the blood sample or tissue sample of the patient compared to a normal standard for $^{33}S$.

3. The method according to claim 1, wherein the method further comprises measuring the level of $^{34}S$ in a blood sample or a tissue sample of the patient and diagnosing cancer in the patient if more than 3.4 times increased level of $^{34}S$ is detected in the blood sample or tissue sample of the patient compared to a normal standard for $^{34}S$.

4. The method according to claim 1, wherein the level of the at least once calcium isotope is greater than 2.8 times the normal standard for the at least one calcium isotope.

* * * * *

UNITED STATES PATENT AND TRADEMARK OFFICE
CERTIFICATE OF CORRECTION

PATENT NO. : 8,771,976 B2
APPLICATION NO. : 12/674425
DATED : July 8, 2014
INVENTOR(S) : Won Cheol Choi Page 1 of 1

It is certified that error appears in the above-identified patent and that said Letters Patent is hereby corrected as shown below:

In the Specification

Column 1, line 25: "isos "equal" +topos" should be -- *isos* "equal" + *topo*s --.

Column 3, line 42: "C." should be -- C --.

Column 3, line 49: "800° C." should be -- 800° C --.

Signed and Sealed this
Thirtieth Day of September, 2014

Michelle K. Lee
*Deputy Director of the United States Patent and Trademark Office*